United States Patent
Baileykobayashi et al.

(10) Patent No.: US 10,421,944 B2
(45) Date of Patent: Sep. 24, 2019

(54) METHOD FOR PRODUCING NEURAL STEM CELLS USING SYNTHETIC PEPTIDE

(71) Applicants: TOAGOSEI CO. LTD., Tokyo (JP); KEIO UNIVERSITY, Tokyo (JP)

(72) Inventors: Nahoko Baileykobayashi, Tsukuba (JP); Kenichi Tanaka, Ryugasaki (JP); Tetsuhiko Yoshida, Tsukuba (JP); Jun Kudo, Tokyo (JP)

(73) Assignees: TOAGOSEI CO. LTD., Tokyo (JP); KEIO UNIVERSITY, Tokyo (JP)

(*) Notice: Subject to any disclaimer, the term of this patent is extended or adjusted under 35 U.S.C. 154(b) by 0 days.

(21) Appl. No.: 15/279,890

(22) Filed: Sep. 29, 2016

(65) Prior Publication Data

US 2017/0088817 A1 Mar. 30, 2017

(30) Foreign Application Priority Data

Sep. 29, 2015 (JP) ................................ 2015-191658

(51) Int. Cl.
  *C12N 5/0797* (2010.01)
(52) U.S. Cl.
  CPC ........ *C12N 5/0623* (2013.01); *C12N 2500/34* (2013.01); *C12N 2501/90* (2013.01); *C12N 2501/998* (2013.01); *C12N 2506/1307* (2013.01)
(58) Field of Classification Search
  CPC combination set(s) only.
  See application file for complete search history.

(56) References Cited

U.S. PATENT DOCUMENTS

| | | | |
|---|---|---|---|
| 2009/0068742 A1 | 3/2009 | Yamanaka | |
| 2009/0325288 A1 | 12/2009 | Koshimizu et al. | |
| 2010/0297758 A1 | 11/2010 | Yoshida et al. | |
| 2012/0035112 A1 | 2/2012 | Yoshida et al. | |
| 2012/0052576 A1 | 3/2012 | Rezania | |
| 2013/0005034 A1 | 1/2013 | Yoshida et al. | |
| 2014/0051171 A1 | 2/2014 | Christensen et al. | |
| 2015/0126434 A1 | 5/2015 | Kobayashi et al. | |

FOREIGN PATENT DOCUMENTS

| | | | | |
|---|---|---|---|---|
| EP | 2 263 705 A1 | 12/2010 | | |
| JP | 2009-165481 A | 7/2009 | | |
| JP | 2009-215191 A | 9/2009 | | |
| JP | 2013-535973 A | 9/2013 | | |
| WO | 2005/040391 A1 | 5/2005 | | |
| WO | 2007/126077 A1 | 11/2007 | | |
| WO | 2009/093692 A1 | 7/2009 | | |
| WO | 2010/117079 A1 | 10/2010 | | |
| WO | WO 2010/117079 | * | 10/2010 | |
| WO | 2013/062140 A1 | 5/2013 | | |
| WO | 2013/180011 A1 | 12/2013 | | |
| WO | WO 2015/098962 | * | 7/2015 | ............. C07K 14/47 |
| WO | 2016/175303 A1 | 11/2016 | | |

OTHER PUBLICATIONS

Patel and Yang, Stem Cell Rev and Rep (2010) 6:367-380.*
Thomas Vierbuchen et al; "Direct conversion of fibroblasts to functional neurons by defined factors;" Nature; Feb. 25, 2010; vol. 463; pp. 1035-1041.
Zhiping P. Pang et al; "Induction of human neuronal cells by defined transcription factors;" Nature; Aug. 11, 2011; vol. 476; pp. 220-223.
Tania Aguado et al; The endocannabinoid system promotes astroglial differentiation by acting on neural progenitor cells.; The Journal of Neuroscience; Feb. 1, 2006; vol. 26; pp. 1551-1561.
Mar. 31, 2015 Search Report issued in Japanese Patent Application No. 2014-084144.
Mar. 31, 2015 Written Opinion issued in Japanese Patent Applciation No. 2014-084144.
Shariati Ali M.S. "APLP2 regulates neuronal stem cell differentiation during cortical development". Journal of Cell Science, vol. 126, p. 1268-1277, Mar. 2013.
Freude, Kristine K., "Soluble Amyloid Precursor Protien Induces Rapid Neural Differentiation of Human embyonic stem cells". J. Biol. Chem., vol. 286, No. 27, p. 24264-24274, 2011.
Huang Hsiang-Po, Factors from Human Embryonic Stem Cell-deroved Fibroblast-like Cells Promote topology-dependent Hepatic Differentiation in Primate Embryonic and Induced Pluripotent Stem Cells. J. Biol. Chem., vol. 285, No. 43, p. 33510-33519, 2010.
Kahoko Umeda, "ES Saibo kara Suizo Kanzo o tsukuru". Chemical Education, vol. 57, No. 10, p. 446-449, 2009.
Song, Zhihua et al, "Efficient generation of hepatocyte-like cells from human induced pluripotent stem cells", 2009, Cell Research, vol. 19, pp. 1233-1242.
Shiraki, Nobuaki et al, "Efficient Differentiation of Embryonic Stem Cells into Hepatic Cells In Vitro Using a Feeder-Free Basement Membrane Substratum", Aug. 2011, Plos One, vol. 6, No. 8, e24228, pp. 1-10.
May 16, 2017 Search Report issued in European Patent Application No. 14873237.3.
Karim Si-Tayeb et al., "Highly efficient generation of human hepatocyte-like cells from induced pluripotent stem cells," Hepatology, Wiley, vol. 51, No. 1. Jan. 1, 2010, pp. 297-305.

(Continued)

*Primary Examiner* — Kimberly Ballard
*Assistant Examiner* — Stacey N MacFarlane
(74) *Attorney, Agent, or Firm* — Oliff PLC

(57) ABSTRACT

The composition for producing neural stem cells provided by the present invention contains an artificially synthesized synthetic peptide having a neural stem cell-inducing peptide sequence that induces neural stem cells from fibroblasts, and one or two or more pharmaceutically acceptable carriers. The neural stem cell-inducing peptide sequence is any of (i) an amino acid sequence constituting a signal peptide of any protein belonging to the amyloid precursor protein (APP) family, (ii) a partial amino acid sequence of the amino acid sequence of (i), and (iii) a modified amino acid sequence of the amino acid sequence of (i) or (ii).

6 Claims, 4 Drawing Sheets

Specification includes a Sequence Listing.

(56) References Cited

OTHER PUBLICATIONS

Kobayashi N.et al., "A novel peptide for triggering differentiation of hepatocyte-like cells from human induced pluripotent stem cells," FEBS Journal, [Online] vol. 281, Suppl. No. 1, Sun-449, Sep. 30, 2014.
Oct. 3, 2017 Office Action issued in U.S. Appl. No. 15/107,726.
Calbiochem. TPB. Datasheet [online]. Copyright 2017. EMD Millipore Corporation [retrieved on Sep. 19, 2017]. Retrieved from the Internet: <URL: http(s)://www.emdmillipore.com/US/en/product/a-Amyloid-Precursor-Protein-Modulator—CAS-497259-23-1—Calbiochem, EMD_BIO-56574CI>p. 1.
Sprecher, C.A. er al. 1993. Molecular cloning of the cDNA for a human amyloid precursor protein homolog: evidence for a multigene family. Biochemistry 32: 4481-4486. specif. pp. 4481, 4483.
U.S. Appl. No. 15/107,726, filed Jun. 23, 2016, in the name of Kenichi Tanaka et al.

\* cited by examiner

METHOD FOR PRODUCING NEURAL STEM CELLS USING SYNTHETIC PEPTIDE

BACKGROUND OF THE INVENTION

1. Field of the Invention

The present invention relates to a composition for use in producing neural stem cells from fibroblasts. In particular, it relates to a synthetic peptide capable of inducing differentiation of fibroblasts into neural stem cells, or in other words to a synthetic peptide for use in the aforementioned composition. It also relates to a method for producing neural stem cells from fibroblasts using this synthetic peptide (or composition).

The priority claim for this application is based on Japanese Patent Application No. 2015-191658 submitted on Sep. 29, 2015, and the entire contents of that application are incorporated herein by reference.

2. Description of the Related Art

One issue in the field of regenerative medicine is the regeneration and restoration of neural function lost due to various kinds of neurological disease, injury and the like.

For example, methods are being explored of transferring nerve cells produced by in vitro culture into an affected area to replace lost nerve cells. However, even when nerve cells that have already undergone axon elongation are transferred into an affected area (into central nervous system tissue such as brain, for example), it can be difficult to reconstruct the neural network before the injury. In particular, because central nervous system tissue achieves and maintains neural function by constructing a physiological environment involving interactions between nerve cells and various other cells (such as astrocytes), it can be difficult to restore neural function by replenishing only the nerve cells.

Techniques for regenerating and restoring neural function using neural stem cells are therefore much anticipated. For example, it is hoped that methods can be developed of restoring neural function by introducing neural stem cells into an affected area (into central nervous system tissue such as brain, for example) or using the regenerative ability of endogenous neural stem cells, and inducing these to differentiate into the necessary cells (such as nerve cells or astrocytes) in vivo (typically in an affected area) to thereby replace lost cells and reconstruct the neural network and physiological environment.

Methods of obtaining neural stem cells that can be transferred into affected areas include isolating the cells from brain tissue, or inducing them from embryonic stem (ES) cells, induced pluripotent stem (iPS) cells and other pluripotent stem cells. However, methods using neural stem cells in the brain and methods of inducing neural stem cells from ES cells are difficult to implement due to ethical issues and problems of rejection and the like. Moreover, methods of inducing neural stem cells from iPS cells still face practical issues of safety, efficiency and cost.

In recent years, therefore, attention has focused on the development of so-called "direct reprogramming" techniques, in which target cells (such as neural stem cells) are prepared directly from somatic cells without an intermediate step of preparing pluripotent stem cells (such as iPS cells). For example, Japanese Translation of PCT Application No. 2013-535973, Nature 463, 2010, pp. 1035-1041 and Nature 476, 2011, pp. 220-223 all describe techniques for transdifferentiating (fate transforming) somatic cells into neural stem cells (or nerve cells) by introducing specific genes into the somatic cells, or in other words techniques of direct reprogramming neural stem cells (or nerve cells) from somatic cells.

SUMMARY OF THE INVENTION

Because the methods of Japanese Translation of PCT Application No. 2013-535973, Nature 463, 2010, pp. 1035-1041 and Nature 476, 2011, pp. 220-223 above are methods for transdifferentiating somatic cells into neural stem cells (or nerve cells) by introducing specific genes into specific somatic cells (direct reprogramming), there is a risk that the introduced gene may be incorporated into the genome (risk of gene insertion), accompanied by a consequent risk of tumorigenesis, and there are also concerns about the complexity of gene introduction operations, efficiency of induction of the neural stem cells (or nerve cells) and the like.

It is an object of the present invention to provide a method whereby, unlike in conventional methods of producing neural stem cells by direct reprogramming, neural stem cells are prepared (directly) from fibroblasts using an artificially synthesizable peptide with a relatively short chain length. Other objects are to provide a synthetic peptide contributing to the object of transdifferentiation (or in other words direct reprogramming) of neural stem cells from fibroblasts, and to provide a composition containing this synthetic peptide (in other words, a composition for producing neural stem cells, to be used in producing neural stem cells from fibroblasts).

The inventors conducted exhaustive research into various peptides with the aim of obtaining a peptide that could be used in a method of producing neural stem cells from fibroblasts. Surprisingly, we discovered that a synthetic peptide synthesized so as to contain all or part of an amino acid sequence (hereunder called a signal peptide sequence) constituting a signal peptide of any protein in the amyloid precursor protein (APP) family, a family of proteins previously known for functions totally unrelated to cell reprogramming and differentiation induction, has the ability (hereunder also called "neural stem cell-inducing activity") to transdifferentiate (or in other words direct reprogram) fibroblasts into neural stem cells (typically nestin-expressing cells, such as cells co-expressing nestin and glial fibrillary acidic protein (GFAP)), thereby perfecting the present invention.

Typical examples of proteins in the APP family include amyloid precursor protein (APP) and two amyloid precursor-like proteins related to APP, amyloid precursor-like protein 1 (APLP1) and amyloid precursor-like protein 2 (APLP2).

A composition to be used for producing neural stem cells from fibroblasts (composition for producing neural stem cells) is provided by the present invention. This composition contains an artificially synthesized synthetic peptide having a neural stem cell-inducing peptide sequence that induces neural stem cells from fibroblasts, and one or two or more pharmaceutically acceptable carriers (for example, at least one kind of base that contributes to improving the stability of the peptide, or saline or various buffers and other liquid media). The neural stem cell-inducing peptide sequence is any of the amino acid sequences shown in (i) to (iii) below:

(i) an amino acid sequence constituting a signal peptide of any protein belonging to the amyloid precursor protein (APP) family;

(ii) a partial amino acid sequence having some of the continuous amino acid residues of the amino acid sequence of (i) above; and (iii) a modified amino acid sequence formed by substituting, deleting and/or adding (preferably by conservative substitution) one, two or three amino acid residues in the amino acid sequence of (i) or (ii) above.

In this Description, a synthetic peptide having a neural stem cell-inducing peptide sequence (that is, a synthetic peptide having neural stem cell-inducing activity) is also called a "neural stem cell-inducing synthetic peptide".

In this Description, moreover, the general term for an amino acid sequence constituting a signal peptide of any protein in the APP family, or a partial amino acid sequence of that signal peptide sequence (that is, a partial sequence consisting of some of the continuous amino acids of that signal peptide sequence) is "APP signal peptide-associated sequence".

Because the composition for producing neural stem cells disclosed here contains a neural stem cell-inducing synthetic peptide, target fibroblasts can be induced to differentiate into neural stem cells (typically nestin expressing cells, such as cells co-expressing nestin and GFAP) by the simple action of supplying the composition for producing neural stem cells to the target fibroblasts (typically, to the medium of a culture of such cells) for example.

Moreover, the neural stem cell-inducing synthetic peptide contained in the composition for producing neural stem cells disclosed here has a simple structure (typically, a straight-chain peptide structure), and can easily be produced artificially by chemical synthesis (typically biosynthesis). Consequently, the desired amount of the composition for producing neural stem cells can be prepared easily or at low cost. Moreover, using the composition for producing neural stem cells disclosed here it is possible to induce neural stem cells from fibroblasts without using large quantities of expensive cytokines and other liquid factors (typically, as a substitute for liquid factors).

Using the composition for producing neural stem cells disclosed here, it is possible to induce neural stem cells from fibroblasts without introducing any exogenous genes. Therefore, there is no risk of exogenous genes being incorporated into genome DNA.

In a preferred embodiment of the composition for producing neural stem cells disclosed here, the protein belonging to the amyloid precursor protein family is amyloid precursor protein, amyloid precursor-like protein 1 or amyloid precursor-like protein 2.

Amyloid precursor protein, amyloid precursor-like protein 1 and amyloid precursor-like protein 2 are all typical proteins belonging to the APP family. Synthetic peptides containing APP signal peptide-associated sequences of these proteins and modified amino acid sequences of these sequences are typical examples of peptides having neural stem cell-inducing activity, and can be used favorably for implementing the present invention.

In a preferred embodiment of the composition for producing neural stem cells disclosed here, the neural stem cell-inducing peptide sequence contained in the neural stem cell-inducing synthetic peptide is selected from the amino acid sequences shown in i) to vi) below:

i) the amino acid sequence of SEQ ID NO:1 below:
MAATGTAAAAATGRLLLLLLVGLTAPALA (SEQ ID NO:1); or a partial continuous amino acid sequence out of the amino acid sequence shown by SEQ ID NO:1 that is a partial amino acid sequence having at least the amino acid sequence shown by SEQ ID NO:16; or a modified amino acid sequence formed by substituting, deleting and/or adding one, two or three amino acid residues in these amino acid sequences;

ii) the amino acid sequence of SEQ ID NO:2 below:
MAATGTAAAAATGKLLVLLLLGLTAPAAA (SEQ ID NO:2); or a partial continuous amino acid sequence out of the amino acid sequence shown by SEQ ID NO:2 that is a partial amino acid sequence having at least the amino acid sequence shown by SEQ ID NO:17; or a modified amino acid sequence formed by substituting, deleting and/or adding one, two or three amino acid residues in these amino acid sequences;

iii) the amino acid sequence of SEQ ID NO:3 below:
MGPASPAARGLSRRPGQPPLPLLLPLLLLLLRAQPAIG (SEQ ID NO:3); or a partial continuous amino acid sequence out of the amino acid sequence shown by SEQ ID NO:3 that is a partial amino acid sequence having at least the amino acid sequence shown by SEQ ID NO:18; or a partial continuous amino acid sequence out of the amino acid sequence shown by SEQ ID NO:3 that is a partial amino acid sequence having at least the amino acid sequence shown by SEQ ID NO:19; or a modified amino acid sequence formed by substituting, deleting and/or adding one, two or three amino acid residues in these amino acid sequences;

iv) the amino acid sequence of SEQ ID NO:4 below:
MGPTSPAARGQGRRWRPPLPLLLPLSLLLLRAQLAVG (SEQ ID NO:4); or a partial continuous amino acid sequence out of the amino acid sequence shown by SEQ ID NO:4 that is a partial amino acid sequence having at least the amino acid sequence shown by SEQ ID NO:20; or a partial continuous amino acid sequence out of the amino acid sequence shown by SEQ ID NO:4 that is a partial amino acid sequence having at least the amino acid sequence shown by SEQ ID NO:21; or a modified amino acid sequence formed by substituting, deleting and/or adding one, two or three amino acid residues in these amino acid sequences;

v) the amino acid sequence of SEQ ID NO:5 below:
MLPGLALLLLAAWTARA (SEQ ID NO:5); or a partial continuous amino acid sequence out of the amino acid sequence shown by SEQ ID NO:5 that is a partial amino acid sequence having at least the amino acid sequence shown by SEQ ID NO:22; or a partial continuous amino acid sequence out of the amino acid sequence shown by SEQ ID NO:5 that is a partial amino acid sequence having at least the amino acid sequence shown by SEQ ID NO:23; or a modified amino acid sequence formed by substituting, deleting and/or adding one, two or three amino acid residues in these amino acid sequences; and vi) the amino acid sequence of SEQ ID NO:6 below:
MLPSLALLLLAAWTVRA (SEQ ID NO:6); or a partial continuous amino acid sequence out of the amino acid sequence shown by SEQ ID NO:6 that is a partial amino acid sequence having at least the amino acid sequence shown by SEQ ID NO:24; or a partial continuous amino acid sequence out of the amino acid sequence shown by SEQ ID NO:6 that is a partial amino acid sequence having at least the amino acid sequence shown by SEQ ID NO:25; or a modified amino acid sequence formed by substituting, deleting and/or adding one, two or three amino acid residues in these amino acid sequences.

The amino acid sequences shown by SEQ ID NOS:1 to 6 are typical examples of amino acid sequence constituting signal peptides of proteins in the APP family. Moreover, the amino acid sequences shown by SEQ ID NOS:1 to 6 and the partial amino acid sequences of these amino acid sequences shown here (partial amino acid sequences having at least the amino acid sequences represented by SEQ ID NOS:16 to 25) are typical examples of APP signal peptide-associated sequences. Peptides containing these amino acid sequences or modified amino acid sequences thereof are peptides having high neural stem cell-inducing activity, and can be used favorably in implementing the present invention.

In a preferred embodiment of the composition for producing neural stem cells disclosed here, the neural stem cell-inducing synthetic peptide has a transmembrane peptide sequence at the N-end or C-end of the amino acid sequence of the neural stem cell-inducing peptide sequence.

By adding the neural stem cell-inducing synthetic peptide having such a transmembrane peptide sequence to target fibroblasts (typically to medium), it is possible to efficiently transfer the neural stem cell-inducing peptide sequence from the outside (outside the cell membrane) to the cell interior of the fibroblasts.

In a preferred embodiment of the composition for producing neural stem cells disclosed here, the neural stem cell-inducing synthetic peptide has the following amino acid sequence as the transmembrane peptide sequence;

KKRTLRKNDRKKR (SEQ ID NO:7).

The amino acid sequence disclosed here as SEQ ID NO:7 is a typical example of an amino acid sequence constituting a transmembrane peptide, and can be used favorably in implementing the present invention.

In the preferred embodiment of the composition for producing neural stem cells disclosed here, the total number of amino acid residues constituting the neural stem cell-inducing synthetic peptide is 100 or fewer. More preferably, the total number of amino acid residues constituting the neural stem cell-inducing synthetic peptide is 50 or fewer.

A peptide comprising such a short peptide chain has high structural stability (such as protease resistance), and excellent handling and storage characteristics. Moreover, a peptide with such a short peptide chain is easy to chemically synthesize, and can be produced (obtained) with relatively low production costs. Consequently, this peptide can be used favorably as a component of the composition for producing neural stem cells disclosed here. Moreover, reduced neural stem cell production costs, improved neural stem cell production efficiency and the like can be achieved by using this neural stem cell-inducing synthetic peptide to produce neural stem cells.

In the preferred embodiment of the composition for producing neural stem cells disclosed here, the neural stem cell-inducing synthetic peptide has the following amino acid sequence:

LLLLLLVGLTAPAGKKRTLRKNDRKKR (SEQ ID NO:26).

This neural stem cell-inducing synthetic peptide is particularly efficient at inducing neural stem cells from fibroblasts. It has excellent ability to induce neural stem cells from human-derived fibroblasts. Thus, this peptide can be used favorably as a component of the composition for producing neural stem cells disclosed here.

In the preferred embodiment of the composition for producing neural stem cells disclosed here, the fibroblasts are fibroblasts from human skin.

Neural stem cells produced from human cells are extremely valuable in the medical fields (particularly in the fields of regenerative medicine, new drug development, basic medicine and the like). Fibroblasts from skin are also preferable as the target cells because fibroblasts are abundantly present in skin (particularly dermis), allowing the necessary quantity of cells to be obtained relatively easily.

Another aspect of the present invention provides a method for producing neural stem cells from fibroblasts either in vitro or in vivo. This method for producing neural stem cells includes preparing a cell culture containing the target fibroblasts, and supplying an artificially produced synthetic peptide to this cell culture. The synthetic peptide here is a synthetic peptide having a neural stem cell-inducing peptide sequence that induces neural stem cells from fibroblasts. This neural stem cell-inducing peptide sequence is any of the amino acid sequences shown in (i) to (iii) below:

(i) an amino acid sequence constituting a signal peptide of any protein belonging to the amyloid precursor protein (APP) family;

(ii) a partial amino acid sequence having some of the continuous amino acid residues of the amino acid sequence of (i) above; and (iii) a modified amino acid sequence formed by substituting, deleting and/or adding (preferably by conservative substitution) one, two or three amino acid residues in the amino acid sequence of (i) or (ii) above.

In other words, the method for producing neural stem cells disclosed here includes preparing a cell culture containing target fibroblasts, and supplying any of the neural stem cell-inducing synthetic peptides disclosed here (that is, any of the compositions for producing neural stem cells disclosed here) to the cell culture.

The method for producing neural stem cells disclosed here can induce neural stem cells (typically nestin-expressing cells, such as cells co-expressing nestin and GFAP) from fibroblasts by the simple action of supplying a synthetic peptide having a neural stem cell-inducing peptide sequence to target fibroblasts (typically, to medium in which such cells are cultured). Specifically, it can induce neural stem cells from fibroblasts (directly prepare neural stem cells from fibroblasts) without an intervening step of preparing pluripotent stem cells (such as iPs cells). Consequently, neural stem cells (typically nestin-expressing cells, such as cells co-expressing nestin and GFAP) can be produced more quickly and efficiently than with methods in which suitable somatic cells are first reprogrammed (initialized) to become pluripotent stem cells, and these pluripotent stem cells are then induced to differentiate into neural stem cells. This method for producing neural stem cells is also preferable because it can induce neural stem cells from fibroblasts with high reproducibility.

Because this method for producing neural stem cells does not require gene introduction, moreover, there is no risk that an endogenous gene will be inserted into the genome of the resulting neural stem cells. This method also avoids the complex operations of introducing specific genes into target cells, and reduces the costs associated with such gene introduction.

In a preferred embodiment of the method for producing neural stem cells disclosed here, the fibroblasts are fibroblasts from human skin. As discussed above, methods of producing neural stem cells from human-derived cells are extremely valuable in the medical fields. Moreover, the desired quantity of fibroblasts can be secured relatively easily if the target cells are dermal (particularly epidermal) fibroblasts.

DESCRIPTION OF THE PREFERRED EMBODIMENTS

Figure 1:
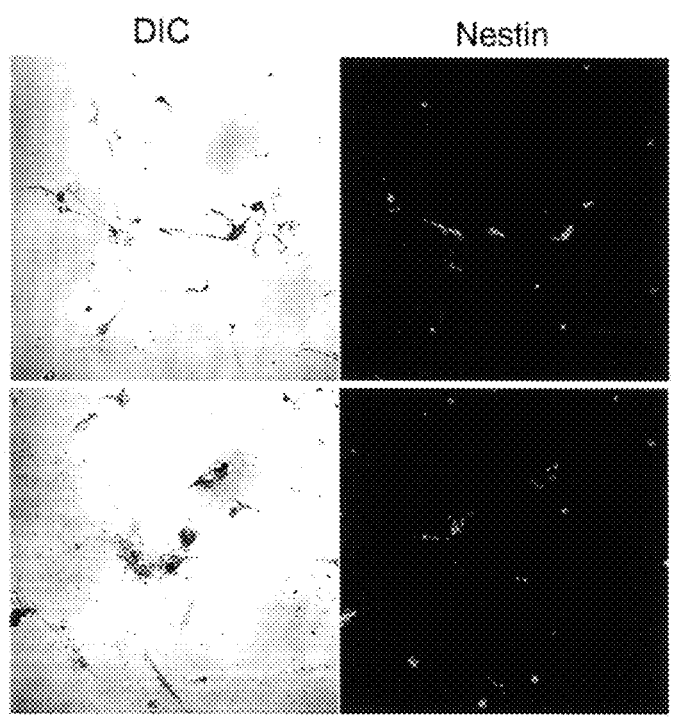
FIG. 1 shows microscope photographs (images) of fibroblast morphology and nestin protein expression after 18 days of culture in the presence of a neural stem cell-inducing synthetic peptide (Sample 1) of one embodiment. The photographs (images) in the DIC column (left column) are optical microscope photographs (images) showing fibroblast morphology, while the photographs (images) in the Nestin column (right column) are fluorescence microscope photographs (images) showing expression of nestin in the same fibroblasts (same visual field)

Preferred embodiments of the present invention are explained below. Matters other than those specifically mentioned in this Description (such as the primary structure and chain length of the synthetic peptide disclosed here) that are necessary for implementing the invention (such as peptide chemical synthesis methods, cell culture methods, and general matters relating to preparation of a pharmacological composition having the peptide as an ingredient) can be understood as design matters by a person skilled in the art based on conventional technology in the fields of cell engineering, physiology, medicine, pharmacology, organic chemistry, biochemistry, genetic engineering, protein engineering, molecular biology, genetics and the like. The present invention can be implemented based on the content disclosed in this Description and technical common knowledge in these fields. In the explanations below, amino acids are sometimes designated by single-letter abbreviations based on the nomenclature for amino acids in the IUPAC-IUB guidelines (but 3-letter abbreviations are used in the sequence tables).

Moreover, the entire contents of all literature cited in this Description is herein incorporated by reference.

In this Description, a "synthetic peptide" is not a peptide chain that can exist stably in nature by itself independently, but is a peptide fragment that has been produced by artificial chemical synthesis or biosynthesis (that is, based on genetic engineering), and can exist stably in a predetermined composition (such as a composition for producing neural stem cells, for use in producing neural stem cells from fibroblasts).

In this Description, moreover, the term "peptide" refers to an amino acid polymer having multiple peptide bonds, and is not limited as to the number of amino acid residues in the peptide chain, but typically this is a peptide with a relatively low molecular weight, such as one having a total of 200 or fewer (preferably 100 or fewer, such as 50 or fewer) amino acid residues.

Unless otherwise specified, in this Description the term "amino acid residue" encompasses the N-terminal amino acid and C-terminal amino acid of the peptide chain.

In the amino acid sequences described in this Description, the left end of the sequence is always the N-end and the right end is the C-end.

A "modified amino acid sequence" of a predetermined amino acid sequence in this Description is an amino acid sequence formed by substituting, deleting and/or adding (inserting) one or more amino acid residues, such as one, two or three amino acid residues, without detracting from the function of the predetermined amino acid sequence (for example, the neural stem cell-inducing activity of the neural stem cell-inducing synthetic peptide, or the transmembrane property of the transmembrane peptide sequence discussed below). Typical examples of modified amino acid sequences as defined in this Description Sequences include those produced by so-called conservative amino acid replacement of one, two or three amino acid residues (for example, sequences produced by substitution of one basic amino acid residue for another basic amino acid residue, such as mutual substitution of lysine and arginine residues) and sequences produced by adding (inserting) or deleting one, two or three amino acid residues in a predetermined amino acid sequence and the like. Therefore, the neural stem cell-inducing synthetic peptide disclosed here encompasses not only synthetic peptides comprised of amino acid sequences identical to the amino acid sequences of the sequence ID numbers, but also amino acid sequences produced by substitution (such as conservative replacement), deletion and/or addition of one, two or three amino acid residues in the amino acid sequences of the sequence ID numbers, which are synthetic peptides comprising amino acid sequences exhibiting similar neural stem cell-inducing activity.

In this Description, a "neural stem cell" is a cell that has self-replicating ability and is capable of differentiating into one, or preferably two or more neural cells, or into tissue or the like composed of these cells. A "neural cell" is defined as a cell constituting the nervous system (central nervous system and peripheral nervous system), and typical examples include nerve cells (so-called neurons) and glial cells (such as astrocytes, oligodendrocytes, and Schwann cells). In this Description, a neural stem cell may be a cell characterized by expressing a gene (neural stem cell marker gene) known to be expressed characteristically in neural stem cells, but this is not a requirement as long as it has the abilities described above.

Typical examples of the neural stem cell marker gene include nestin and GFAP, but are not limited to these as long as the gene is known to be expressed characteristically in neural stem cells. That is, the neural stem cell may be a cell characterized by expressing at least nestin (preferably, both nestin and GFAP). Typically, it is a cell in which the presence of mRNA or a protein (also called a neural stem cell marker protein) that is a gene product of the neural stem cell marker gene (such as nestin, preferably both nestin and GFAP) can be confirmed. Neural stem cells present in the brain in the living body (typically the adult body) have been confirmed to express both nestin and GFAP (The Journal of Neuroscience, Vol. 26, 2006, pp. 1551-1561). Thus, neural stem cells expressing both nestin and GFAP are preferable because they are more similar to neural stem cells in the living brain.

The method for producing neural stem cells (typically nestin-expressing cells, such as cells co-expressing nestin and GFAP) disclosed here is a production method wherein a synthetic peptide having neural stem cell-inducing activity (that is, a neural stem cell-inducing synthetic peptide) is supplied to target fibroblasts (typically, to a culture of these cells). Specifically, the method for producing neural stem cells disclosed here is a method of producing neural stem cells (typically nestin-expressing cells, such as cells co-expressing nestin and GFAP) from fibroblasts by inducing neural stem cells from fibroblasts without an intervening step of preparing pluripotent stem cells, or in other words by transdifferentiating fibroblasts into neural stem cells (or in other words by direct reprogramming of fibroblasts into neural stem cells).

This method for producing neural stem cells is not limited to production of neural stem cells by in vitro culture, and can also be applied to producing neural stem cells or promoting the production of neural stem cells in vivo.

The composition for producing neural stem cells disclosed here is a composition for use in producing neural stem cells (typically nestin-expressing cells, such as cells co-expressing nestin and GFAP) from fibroblasts. Specifically, it is a composition characterized by containing at least one kind of the neural stem cell-inducing synthetic peptide disclosed here as an active ingredient (that is, as a substance involved in inducing differentiation of fibroblasts into neural stem cells).

As discussed above, the neural stem cell-inducing synthetic peptide disclosed here is a synthetic peptide having a neural stem cell-inducing peptide sequence that was discovered by the inventors to be capable of inducing neural stem cells (typically nestin-expressing cells, such as cells co-expressing nestin and GFAP) from fibroblasts when supplied to fibroblasts (typically to a culture of these cells). In other words, the neural stem cell-inducing synthetic peptide is capable of transdifferentiating (that is, directly reprogramming) fibroblasts into neural stem cells.

In the neural stem cell-inducing synthetic peptide disclosed here, the neural stem cell-inducing peptide sequence is selected from the signal peptide sequences of any proteins belonging to the APP family, the partial amino acid sequences of these signal peptide sequences (that is, APP signal peptide-associated sequences), or the modified amino acid sequences of these amino acid sequences.

Typical proteins belonging to the APP family are APP, APLP1 and APLP2. According to the amyloid hypothesis, which is one hypothesis about the onset mechanism of Alzheimer's disease, the APP protein may be called a starting substance for Alzheimer's disease, while the APLP1 and APLP2 proteins are known as analogous proteins of APP.

Signal peptide sequences of proteins in the APP family that can be used favorably in implementing the present invention are shown by SEQ ID NOS:1 to 6.

Specifically, the amino acid sequence of SEQ ID NO:1 is an amino acid sequence comprising a total of 29 amino acid residues constituting a signal peptide of human-derived APLP2.

The amino acid sequence of SEQ ID NO:2 is an amino acid sequence comprising a total of 29 amino acid residues constituting a signal peptide of mouse-derived APLP2.

The amino acid sequence of SEQ ID NO:3 is an amino acid sequence comprising a total of 38 amino acid residues constituting a signal peptide of human-derived APLP1.

The amino acid sequence of SEQ ID NO:4 is an amino acid sequence comprising a total of 37 amino acid residues constituting a signal peptide of mouse-derived APLP1.

The amino acid sequence of SEQ ID NO:5 is an amino acid sequence comprising a total of 17 amino acid residues constituting a signal peptide of human-derived APP.

The amino acid sequence of SEQ ID NO:6 is an amino acid sequence comprising a total of 17 amino acid residues constituting a signal peptide of mouse-derived APP.

The amino acid sequences of SEQ ID NOS:1 to 6 above may be used as is as neural stem cell-inducing peptide sequences when constituting the neural stem cell-inducing synthetic peptide of the present invention.

SEQ ID NOS:1 to 6 above represent signal peptide sequences of APP, APLP1 or APLP2 from mice or humans, but these sequences are only examples, and applicable amino acid sequences are not limited to these. For example, various APP, APLP1 or APLP2 signal peptide sequences from rats, guinea pigs and other rodents, horses, donkeys and other Perissodactyla, pigs, cows and other Artiodactyla, and chimpanzees, orangutans, macaques and other primates (typically mammals) can be used.

Alternatively, a partial amino acid sequence having part of the continuous amino acid residues of a signal peptide sequence of a protein in the APP family (hereunder sometimes called simply a partial amino acid sequence) can also be used as the neural stem cell-inducing peptide sequence. For example, a partial amino acid sequence having at least an amino acid sequence represented by any of SEQ ID NOS:16 to 25 can be used favorably as the neural stem cell-inducing peptide sequence when implementing the present invention.

In this Description, "having at least" means having specific continuous amino acid residues (typically, the amino acid residues of any of SEQ ID NOS:16 to 25) as an essential amino acid sequence, and optionally having other amino acid sequences at the C-end and N-end of this amino acid sequence. That is, this partial amino acid sequence may be an amino acid sequence comprising an additional one, two, three, four or $X_C$ amino acid residues at the C-end and/or one, two, three, four, or $X_N$ amino acid residues at the N-end of specific continuous amino acid residues (typically, the amino acid residues of any of SEQ ID NOS:16 to 25). The number $X_C$ amino acid residue at the C-end is the C-terminal amino acid residue of the full-length signal peptide sequence, and the number $X_N$ amino acid residue at the N-end is the N-terminal amino acid residue of the full-length signal peptide sequence.

Specifically, the amino acid sequence of SEQ ID NOS:16 to 25 are as follows.

The amino acid sequence of SEQ ID NO:16 is a partial amino acid sequence of the amino acid sequence of SEQ ID NO:1, comprising 13 continuous amino acid residues from the No. 15 leucine residue to the No. 27 alanine residue counting from the N-terminal amino acid residue of that amino acid sequence.

The amino acid sequence of SEQ ID NO:17 is a partial amino acid sequence of the amino acid sequence of SEQ ID NO:2, comprising 12 continuous amino acid residues from the No. 16 leucine residue to the No. 27 alanine residue counting from the N-terminal amino acid residue of that amino acid sequence.

The amino acid sequence of SEQ ID NO:18 is a partial amino acid sequence of the amino acid sequence of SEQ ID NO:3, comprising 13 continuous amino acid residues from the No. 19 proline residue to the No. 31 leucine residue counting from the N-terminal amino acid residue of that amino acid sequence.

The amino acid sequence of SEQ ID NO:19 is a partial amino acid sequence of the amino acid sequence of SEQ ID NO:3, comprising 13 continuous amino acid residues from the No. 26 leucine residue to the No. 38 glycine residue counting from the N-terminal amino acid residue of that amino acid sequence.

The amino acid sequence of SEQ ID NO:20 is a partial amino acid sequence of the amino acid sequence of SEQ ID NO:4, comprising 13 continuous amino acid residues from the No. 18 proline residue to the No. 30 leucine residue counting from the N-terminal amino acid residue of that amino acid sequence.

The amino acid sequence of SEQ ID NO:21 is a partial amino acid sequence of the amino acid sequence of SEQ ID NO:4, comprising 13 continuous amino acid residues from the No. 25 leucine residue to the No. 37 glycine residue counting from the N-terminal amino acid residue of that amino acid sequence.

The amino acid sequence of SEQ ID NO:22 is a partial amino acid sequence of the amino acid sequence of SEQ ID NO:5, comprising 14 continuous amino acid residues from the No. 1 methionine residue to the No. 14 threonine residue counting from the N-terminal amino acid residue of that amino acid sequence.

The amino acid sequence of SEQ ID NO:23 is a partial amino acid sequence of the amino acid sequence of SEQ ID NO:5, comprising 15 continuous amino acid residues from the No. 3 proline residue to the No. 17 alanine residue counting from the N-terminal amino acid residue of that amino acid sequence.

The amino acid sequence of SEQ ID NO:24 is a partial amino acid sequence of the amino acid sequence of SEQ ID NO:6, comprising 14 continuous amino acid residues from the No. 1 methionine residue to the No. 14 threonine residue counting from the N-terminal amino acid residue of that amino acid sequence.

The amino acid sequence of SEQ ID NO:25 is a partial amino acid sequence of the amino acid sequence of SEQ ID NO:6, comprising 15 continuous amino acid residues from the No. 3 proline residue to the No. 17 alanine residue counting from the N-terminal amino acid residue of that amino acid sequence.

The neural stem cell-inducing synthetic peptide disclosed here may be a peptide consisting solely of the neural stem cell-inducing peptide sequence described above, but from the standpoint of improving neural stem cell-inducing activity, it may be a synthetic peptide having a transmembrane peptide sequence at the N-end or C-end of the neural stem cell-inducing peptide sequence. A synthetic peptide having a transmembrane peptide sequence can be introduced rapidly from the cell exterior to the cell interior when it is supplied to target cells. Neural stem cell-inducing activity can be enhanced as a result.

Any amino acid sequence constituting a transmembrane peptide capable of passing through the cell membrane and/or nuclear membrane can be used as this transmembrane sequence, with no particular limitations. Many suitable transmembrane peptide sequences are known, but amino acid sequences (including modified amino acid sequences) associated with NoLS (nucleolar localization signals) are particularly preferable as the amino acid sequence of the transmembrane peptide sequence of the neural stem cell-inducing synthetic peptide. SEQ ID NOS:7 to 15 are desirable examples of such NoLS-associated transmembrane peptide sequences and other transmembrane peptide sequences (including modified amino acid sequences). Specifically, these are as follows.

The amino acid sequence of SEQ ID NO:7 corresponds to a NoLS comprising a total of 13 amino acid residues from the No. 491 amino acid residue to the No. 503 amino acid residue of LIM kinase 2, which is a protein kinase associated with intracellular signaling that is present in human endothelial cells.

The amino acid sequence of SEQ ID NO:8 corresponds to a NoLS comprising a total of 14 amino acid residues from basic fibroblast growth factor (FGF2).

The amino acid sequence of SEQ ID NO:9 corresponds to a NoLS comprising a total of 8 amino acid residues that is contained in a nucleocapsid protein (N protein) of avian infectious bronchitis virus (IBV).

The amino acid sequence of SEQ ID NO:10 corresponds to a NoLS comprising a total of 13 amino acid residues from adenovirus pre-terminal protein (PTP) 1 and PTP2.

The amino acid sequence of SEQ ID NO:11 corresponds to a transmembrane peptide sequence comprising a total of 11 amino acid residues from a protein transduction domain contained in the TAT of human immunodeficiency virus (HIV).

The amino acid sequence of SEQ ID NO:12 corresponds to a transmembrane peptide sequence comprising a total of 11 amino acid residues of a modified protein transduction domain (PTD4) of the same TAT.

The amino acid sequence of SEQ ID NO:13 corresponds to a transmembrane peptide sequence comprising a total of 16 amino acid residues from the ANT of Antennapedia, a mutant form of *Drosophila*.

The amino acid sequence of SEQ ID NO:14 corresponds to a transmembrane peptide sequence comprising a total of 9 arginine residues as a polyarginine.

The amino acid sequence of SEQ ID NO:15 corresponds to a transmembrane peptide sequence comprising a total of 19 amino acid residues from a protein containing a myoblast determination (MyoD) family inhibition domain.

These transmembrane peptide sequences given in the sequence tables are only examples, and applicable transmembrane peptide sequences are not limited to these. Various transmembrane peptide sequences that can be used in implementing the present invention are described in various literature already published at the time of this application. The amino acid sequences of these transmembrane peptide sequences can be easily discovered by ordinary search methods.

The amino acid sequence of SEQ ID NO:7 (including modified amino acid sequences), which is also described in WO 2009/093692, is particularly preferable as a transmembrane peptide sequence. A synthetic peptide exhibiting strong neural stem cell-inducing activity can be obtained by combining this amino acid sequence of SEQ ID NO:7 with the neural stem cell-inducing peptide sequence described above.

Desirable examples of the neural stem cell-inducing synthetic peptide described here include the following amino acid sequence:

LLLLLLVGLTAPAGKKRTLRKNDRKKR (SEQ ID NO:26).

The amino acid sequence of SEQ ID NO:26 is an amino acid sequence comprising a total of 27 amino acid residues, constructed by combining the amino acid sequence of SEQ ID NO:16, which is a partial amino acid sequence of an amino acid sequence (SEQ ID NO:1) constituting a human APLP2 signal peptide, with the LIM kinase 2-derived amino acid sequence (transmembrane peptide sequence) of SEQ ID NO:7 above via one glysine residue (G) as a linker.

Some of the peptide chains (amino acid sequences) of the neural stem cell-inducing synthetic peptide disclosed here can be constructed by suitably combining a neural stem cell-inducing peptide sequence such as that described above with a transmembrane peptide sequence. Either the neural stem cell-inducing peptide sequence or the transmembrane peptide sequence may be disposed at the relative C-end (or N-end). The neural stem cell-inducing peptide sequence and the transmembrane peptide sequence are preferably disposed adjacent to one another. That is, preferably either no amino acid residues not belonging to either sequence part are disposed between the neural stem cell-inducing peptide sequence and the transmembrane peptide sequence, or if such residues are present the number thereof is about one to three. For example, one or more (typically two or three) amino acid residues (such as one or more glycine (G) residues) that function as linkers may be included between the neural stem cell-inducing peptide sequence and the transmembrane peptide sequence.

At least one amino acid residue is preferably amidated in the neural stem cell-inducing synthetic peptide disclosed here. The structural stability of the synthetic peptide (protease resistance for example) can be improved by amidating a carboxyl group of an amino acid residue (typically, the C-terminal amino acid residue of the peptide chain).

The neural stem cell-inducing synthetic peptide may also include a sequence part (amino acid residues) other than the amino acid sequences constituting the neural stem cell-inducing peptide sequence and transmembrane peptide sequence, as long as the neural stem cell-inducing activity is not diminished. This amino acid sequence is not particularly limited, but a sequence capable of maintaining the three-dimensional shapes (typically the straight-chain shapes) of the neural stem cell-inducing peptide sequence and transmembrane peptide sequence is preferable. The total number of amino acid residues constituting the peptide chain of the neural stem cell-inducing synthetic peptide may be 100 or fewer, desirably 60 or fewer, and preferably 50 or fewer. A synthetic peptide of 30 or fewer residues is particularly preferable.

A peptide with such a short chain length is easy to chemically synthesize, allowing the neural stem cell-inducing synthetic peptide to be provided easily. The conformation (three-dimensional structure) of the peptide is not particularly limited as long as the neural stem cell-inducing activity of inducing neural stem cells from fibroblasts is achieved in the environment used (in vitro, typically in medium culturing the target cells), but a straight-chain or helix structure is preferred from the standpoint of inhibiting immunogenicity (antigenicity). Peptides with such structures are unlikely to form epitopes. From this standpoint, the neural stem cell-inducing synthetic peptide used in the method for producing neural stem cells (or the neural stem cell-inducing synthetic peptide applied to the composition for producing neural stem cells) is preferably a straight-chain peptide, and one with a relatively low molecular weight (typically 100 or fewer, such as 60 or fewer, or preferably 50 or fewer, or more preferably 30 or fewer amino acid residues) is desirable.

With a relatively low-molecular-weight neural stem cell-inducing synthetic peptide, a composition for producing neural stem cells having this neural stem cell-inducing synthetic peptide as an active ingredient (that is, a substance involved in inducing neural stem cells from fibroblasts) can be prepared relatively easily and at low cost. A synthetic peptide with the relatively simple structure described above (typically a linear peptide chain) is structurally stable and easy to handle, which also makes it desirable as an active ingredient of composition for producing neural stem cells.

The percentage of the total amino acid sequence made up of the neural stem cell-inducing peptide sequence and transmembrane peptide sequence (that is, the percentage of amino acid residues constituting the neural stem cell-inducing peptide sequence and transmembrane peptide sequence relative to the total amino acid residues constituting the peptide chain) is not particularly limited as long as the neural stem cell-inducing activity of inducing neural stem cells (typically nestin expressing cells, such as cells co-expressing nestin and GFAP) from fibroblasts is not diminished, but a percentage of about 60% or more is desirable, and at least 80% is preferable. 90% or more is particularly preferable. A preferred embodiment is a peptide consisting of a neural stem cell-inducing peptide sequence and a transmembrane peptide sequence (that is, in which these sequences constitute 100% of the total amino acid sequence).

All of the amino acid residues are preferably L-type amino acids in the neural stem cell-inducing synthetic peptide of the present invention, but D-type amino acids may be substituted for some or all of the amino acid residues as long as this does not detract from the neural stem cell-inducing activity of inducing neural stem cells from fibroblasts.

The neural stem cell-inducing synthetic peptide disclosed here can be easily produced by ordinary chemical synthesis methods. For example, a conventional known solid-phase synthesis method or liquid-phase synthesis method may be adopted. Solid-phase synthesis employing Boc (t-butylcarbonyl) or Fmoc (9-fluorenylmethyloxycarbonyl) amino protecting groups is desirable.

For the neural stem cell-inducing synthetic peptide disclosed here, a peptide chain having a desired amino acid sequence and a modified (C-terminal amidated, etc.) part may be synthesized by solid-phase synthesis using a commercial peptide synthesizer (available for example from Intavis AG, Protein Technologies, Inc. and the like).

The neural stem cell-inducing synthetic peptide may also be biosynthesized based on genetic engineering techniques. That is, a polynucleotide (typically DNA) with a nucleotide sequence (including ATG initiation codon) coding for the amino acid sequence of the desired neural stem cell-inducing synthetic peptide can be synthesized. A recombinant vector having a gene expression construct comprising the synthesized polynucleotide (DNA) and various regulatory elements for expressing the amino acid sequence in host cells (including promoters, ribosome binding sites, terminators, enhancers, and various cis-elements for controlling the expression level) can then be constructed to match the host cells.

This recombinant vector is then introduced into predetermined host cells (for example yeast, insect or plant cells) by ordinary methods, and these host cells or a tissue or body containing the cells are then cultured under the predetermined conditions. The target peptide can thus be expressed and produced within the cells. The peptide is isolated from the host cells (or from medium if the peptide is excreted), and refolded, purified and the like as necessary to obtain the target neural stem cell-inducing synthetic peptide.

Methods conventionally used in the field may be adopted as is as the methods for constructing the recombinant vector and methods of introducing the constructed recombinant vector into host cells, and detailed explanations are omitted because these methods are not a special feature of the present invention.

For example, a fusion protein expression system can be used to achieve large-scale and efficient production in host cells. That is, a gene (DNA) coding for the amino acid sequence of the target neural stem cell-inducing synthetic peptide is chemically synthesized, and inserted into a suitable site of a suitable fusion protein expression vector (for example, a glutathione S-transferase (GST) fusion protein expression vector such as the pET series provided by Novagen or the pGEX series provided by Amersham Biosciences). Host cells (typically E. coli) are then transformed with this vector. The resulting transformant is cultured to prepare the target fusion protein. The protein is then extracted and purified. The resulting purified fusion protein is then cleaved with a specific enzyme (protease), and the released target peptide fragment (designed neural stem cell-inducing synthetic peptide) is collected by a method such as affinity chromatography. This may also be refolded as necessary by suitable methods. The neural stem cell-inducing synthetic peptide disclosed here can be produced using such a conventionally known fusion protein expression system (for example, the GST/His system available from Amersham Biosciences can be used).

Alternatively, template DNA for a cell-free protein synthesis system (that is, a synthetic gene fragment containing a nucleotide sequence coding for the amino acid sequence of the neural stem cell-inducing synthetic peptide) can be constructed, and the target polypeptide can then be synthesized in vitro by a so-called cell-free protein synthesis system using various compounds (ATP, RNA polymerase, amino acids, etc.) necessary for peptide synthesis. The papers of Shimizu et al. (Nature Biotechnology, 19, 751-755 (2001)) and Madin et al. (Proc. Natl. Acad. Sci. USA, 97(2), 559-564 (2000)) can be consulted regarding cell-free protein synthesis systems. At the time of this application many companies are already engaged in contract polypeptide production based on the techniques described in these papers, and cell-free protein synthesis kits (for example, the PROTEIOS™ Wheat germ cell-free protein synthesis kit available from CellFree Sciences Co., Ltd.) are commercially available.

Single-stranded and double-stranded polynucleotides containing nucleotide sequences coding for the neural stem cell-inducing synthetic peptide disclosed here and/or nucleotide sequences complementary to these sequences can be easily produced (synthesized) by conventionally known methods. That is, a nucleotide sequence corresponding to the amino acid sequence of the neural stem cell-inducing synthetic peptide can be easily determined and provided by selected the corresponding codons of each of the amino acid residues constituting the designed amino acid sequence. Once the nucleotide sequence has been determined, a (single-stranded) polynucleotide corresponding to the desired nucleotide sequence can be easily obtained with a DNA synthesizer or the like. The resulting single-stranded DNA can then be used as a template to obtain target double-stranded DNA by various enzymatic synthesis methods (typically PCR). The polynucleotide itself may be in the form of either DNA or RNA (mRNA or the like). Either double-stranded or single-stranded DNA may be provided. When single-stranded DNA is provided it may be either a coding strand (sense strand) or a non-coding strand (antisense strand) with a sequence complementary to the coding strand.

As discussed above, the resulting polynucleotide can then be used as a material for constructing a recombinant gene (expression cassette) for producing the neural stem cell-inducing synthetic peptide in various host cells or with a cell-free protein synthesis system.

The neural stem cell-inducing synthetic peptide disclosed here may also be in the form of a salt as long as the neural stem cell-inducing activity is not diminished. For example, it is possible to use an acid addition salt of the peptide, which can be obtained by performing an addition reaction with a commonly used inorganic acid or organic acid by ordinary methods. Another salt (such as a metal salt) is also possible as long as it has the neural stem cell-inducing activity. As used in this Description and in the claims, the term "peptide" encompasses these salts.

A composition containing at least one kind of the neural stem cell-inducing synthetic peptide is also provided by the present invention. This composition is a composition (neural stem cell inducer) capable of inducing neural stem cells (typically nestin expressing cells, such as cells co-expressing nestin and GFAP) from fibroblasts when supplied to such fibroblasts (typically, to medium containing such cells), and can be used to produce neural stem cells (typically nestin expressing cells, such as cells co-expressing nestin and GFAP) from fibroblasts. That is, the present invention provides a composition for producing neural stem cells, to be used for producing neural stem cells from fibroblasts. The composition for producing neural stem cells (neural stem cell inducer) disclosed here may contain various pharmaceutically (medically) acceptable carriers according to the mode of use as long as it can still retain the neural stem cell-inducing synthetic peptide that is the active ingredient (that is, substance involved in inducing neural stem cells from fibroblasts) in such a way that the neural stem cell-inducing activity of the peptide is not diminished. Carriers that are commonly used as diluents, excipients and the like in peptide drugs are preferred as carriers. These may differ appropriately according to the use and form of the composition for producing neural stem cells, but typical examples include water, physiological buffer (such as phosphate-buffered saline (PBS)), and various organic solvents. Aqueous solutions of alcohols (ethanol, etc.) of appropriate concentrations and glycerol, olive oil and other non-drying oils are also possible. Liposomes are also possible. Examples of secondary components that can be included in the composition for producing neural stem cells (neural stem cell inducer) include various fillers, extenders, binders, humectants, surfactants, colorants, perfumes and the like.

The form of the composition for producing neural stem cells (neural stem cell inducer) is not particularly limited. Typical forms include liquids, suspensions, emulsions, aerosols, foams, granules, powders, pills, capsules, ointments, liquid gels and the like. The composition may also be in the form of a freeze-dried preparation or granules for dissolving in saline or a suitable buffer (such as PBS) or the like before use to prepare a medicinal liquid.

The processes used to prepare a medicine (composition) in various forms using the neural stem cell-inducing synthetic peptide (principal ingredient) and various carriers (secondary ingredient) as materials may be consistent with conventional methods, and detailed explanations are omitted because these preparation methods are not a feature of the invention. One source of detailed information regarding formulation methods is "Comprehensive Medical Chemistry, Corwin Hansch Ed., Pergamon Press (1990)". The entire contents of this book are incorporated by reference in this Description.

The fibroblasts to which the composition for producing neural stem cells (neural stem cell-inducing synthetic peptide) disclosed here is applied are not particularly limited, and various kinds of fibroblasts can be induced to become neural stem cells (or induction can be promoted). Examples include cells from humans and non-human animals (typically vertebrates, especially mammals). In general, application to animals (typically mammals) kept as experimental animals (such as mice, rats, guinea pigs, and rabbits), livestock (such as cows, pigs, horses, sheep, and chickens) and pets (such as dogs and cats) is especially useful for industrial purposes. Desirable examples of target mammals include mice, rats, guinea pigs and other rodents, horses, donkeys and other Perissodactyla, pigs, cows and other Artiodactyla, and chimpanzees, orangutans, macaques and other primates (excluding humans) and the like. Also, cells from humans are particularly preferable as target cells because they are valuable in the medical field. In other words, the composition for producing neural stem cells (neural stem cell-inducing synthetic peptide) disclosed here can favorably induce neural stem cells from human-derived fibroblasts, or promote such induction. Fibroblasts from patients are particularly preferable as target cells of the method for producing neural stem cells disclosed here because using such cells is a way of avoiding problems of donor insufficiency and rejection reactions.

Fibroblasts are present in all tissues throughout the body, and are principally present in connective tissue. Fibroblasts normally have strong proliferative ability. Because fibroblasts are typically cells that can be independently cultured, they can be easily cultured (maintained) in an in vitro culture system. That is, because the necessary quantity of fibroblasts can be obtained relatively easily, fibroblasts are preferred as the primary cells (raw material cells) for producing neural stem cells. In other words, the labor, cost and time required to secure raw material cells (target cells) for producing neural stem cells can be diminished (reduced) by applying fibroblasts as the target cells of the composition for producing neural stem cells disclosed here.

For example fibroblasts from the skin (typically dermis), digestive tract, blood vessels, bone, teeth, cartilage, brain, eyes, lungs and other tissues can be used as target cells (raw material cells) for producing neural stem cells.

For example, when the fibroblasts are to be cultured in vitro, cells from skin, blood, teeth, mucous membrane and other tissues are preferable as the fibroblasts targeted by the composition for producing neural stem cells (neural stem cell-inducing synthetic peptide) disclosed here because they can be obtained by a minimally invasive process without seriously damaging the living body. Of these, fibroblasts from skin (typically dermis) are particularly preferable from the standpoint of ease of collection from the living body (low invasiveness) and ease of culture (maintenance) in an in vitro system. The fibroblasts cultured by such in vitro culture are not particularly limited, and may be various kinds of cultured cells such as primary culture cells, passaged cells or a cell line, or may be fibroblasts from tissue (from living tissue) that have been collected from tissue of a living body.

The composition for producing neural stem cells (neural stem cell-inducing synthetic peptide) disclosed here can be combined appropriately with another cell differentiation-inducing factor (differentiation-inducing factor) depending on the type of target cells (original animal or tissue) or the like. Examples of this cell-inducing factor include retinoic acid, various bone morphogenetic factors (factors in the BMP family), TGF-β and other factors in the TGF-β superfamily, basic fibroblast growth factor (bFGF), acidic fibroblast growth factor (aFGF) and other factors in the FGF superfamily, leukemia inhibitory factor (LIF), cholinergic neuronal differentiation factor (CDF), ciliary neurotrophic factor (CNTF) and other factors in the cytokine family, various interleukins, tumor necrosis factor (TNF-α), interferon γ (IFNγ), hepatocyte growth factor (HGF) and the like.

The composition for producing neural stem cells (neural stem cell-inducing synthetic peptide) disclosed here can be used by a method and at a dosage suited to its form and object.

For example, when the aim is to induce neural stem cells from fibroblasts (such as human-derived fibroblasts) cultured (passaged) in vitro, an appropriate amount of the composition for producing neural stem cells (that is, neural stem cell-inducing synthetic peptide contained in this composition) disclosed here can be applied to the fibroblasts targeted for induction (typically, a cell culture containing those cells) by adding it to the medium at any stage of the culture process (such as simultaneously with the beginning of culture, at an early stage after the beginning of culture, or after a specific period of culture (proliferation) or passaging). The added amount and the number of additions are not particularly limited, and may be differ depending on conditions such as the type of culture cells, the cell density (cell density at beginning of culture), the number of passages, culture conditions, the type of medium and the like. For example, the composition (peptide) is preferably added one to multiple times (such as at the beginning of culture, and additionally at the time of each cell passage and medium exchange) so that the neural stem cell-inducing synthetic peptide concentration in medium is in the range of about 0.1 $\mu M$ to 100 or preferably 0.5 $\mu M$ to 20 $\mu M$ (such as 1 $\mu M$ to 10 $\mu M$).

The culture conditions for culturing the fibroblasts (typically, a cell culture containing these cells) to which the neural stem cell-inducing synthetic peptide has been supplied may be similar to normal conditions for culturing those fibroblasts, or these cultures with appropriate modifications. Regarding the culture temperature, a normal culture temperature for culturing fibroblasts from mammals may be adopted when preparing neural stem cells from mammalian fibroblasts. The optimal temperature conditions will differ depending on the type of fibroblasts and their condition and the like, but typically in the case of mammalian cells, the temperature may be set appropriately within the range of 25° C. to less than 37° C. (preferably 25° C. to 35° C., more preferably 30° C. to 35° C.). The medium used in culture may be medium that is similar in composition to medium normally used for culturing the target fibroblasts for example, or medium that is similar in composition to medium used for culturing neural stem cells, without any particular limitations. The humidity and $CO_2$ concentration inside the incubator may also be similar to those used for culturing the target differentiated cells (for example, 5% $CO_2$, RH 95% or more), without any particular limitations.

The culture time of the fibroblasts to which the neural stem cell-inducing synthetic peptide has been supplied (typically, a cell culture containing these fibroblasts) is not particularly limited as long as it is sufficient to allow induction (that is, direct reprogramming) of neural stem cells from the fibroblasts. This culture time is not particularly limited because it may differ according to the type of fibroblasts, the state of the cells (cell density (cell density at beginning of culture), the number of passages, culture conditions, the type of medium) and other conditions, but is generally shorter than the time required to induce differentiation of neural stem cells from pluripotent stem cells after preparing pluripotent stem cells (typically iPS cells) from fibroblasts. For example, in one embodiment of the method for producing neural stem cells disclosed here, neural stem cells can be obtained about 15 days (typically 18 days, such as 20 days, or generally 25 days) after the neural stem cell-inducing synthetic peptide (composition for producing neural stem cells) is supplied to the target fibroblasts. On the other hand, about one month is generally required to prepare pluripotent stem cells from fibroblasts and other somatic cells, and about two months to induce differentiation of neural stem cells from pluripotent stem cells. With the method for producing neural stem cells disclosed here, neural stem cells can be prepared in a shorter amount of time than when obtaining pluripotent stem cells and then preparing neural stem cells.

Moreover, the method for producing neural stem cells disclosed here includes the sorting (isolation) of neural stem cells from a cell culture of cells that have been cultured for a specific amount of time after being supplied with the composition for producing neural stem cells (neural stem cell-inducing synthetic peptide) disclosed here. A cell population with a high proportion (purity) of neural stem cells as a percentage of all cells can be produced by collecting these sorted (isolated) neural stem cells. The method for producing neural stem cells is not limited to production of neural stem cells by in vitro culture, and can be applied to producing neural stem cells or promoting production of neural stem cells in vivo. That is, the composition for producing neural stem cells (neural stem cell-inducing synthetic peptide) disclosed here can be administered in vivo to produce neural stem cells, which can then be sorted (collected, isolated) from the living body.

The sorting of neural stem cells from a cell culture containing such neural stem cells can be accomplished by an appropriate conventional cell sorting method using a characteristic property (marker, label, indicator) of neural stem cells.

The characteristic property of the neural stem cells is not particularly limited as long as it is a characteristic that can be used to distinguish neural stem cells from cells other than neural stem cells that may be present in the cell culture. Examples include expression of a gene that is characteristic of neural stem cells (typically, a gene expressed specifically (selectively) in neural stem cells, in other words a so-called neural stem cell marker gene), or a physiological property of neural stem cells (proliferation, adhesiveness, migration, cell division properties, nutritional requirements, etc.). Examples of the neural stem cell marker gene include nestin and GFAP. Neural stem cells can be sorted satisfactorily from a cell culture of neural stem cells using a gene product of these marker genes (typically mRNA or a protein (marker protein)) as a marker. Because the presence of such mRNA or proteins can be distinguished by relatively easy methods, they can be used favorably in implementing the present invention. Proteins are particularly preferable because they can be distinguished by immunological methods using antibodies that recognize the proteins (methods using antigen-antibody reactions). For example, the nestin protein can be labeled with a fluorescent labeled anti-nestin antibody, and neural stem cells can be distinguished using this label as a benchmark.

The method of sorting the neural stem cells is not particularly limited, and various cell sorting methods can be used to sort the neural stem cells. Examples include cell sorting using a fluorescence-activated cell sorter (FACS), cell sorting using a MACS™ magnetic cell separator, cell sorting under a microscope, cell sorting using optical tweezers, cell sorting using various columns, cell sorting using antigen-antibody reactions, cell sorting using cell staining, cell sorting using labeling by specific gene introduction, cell sorting using physiological properties of the cells (proliferation, adhesiveness, migration, cell division properties, nutritional requirements, etc.) and the like. Cell sorting devices using FACS, MACS and optical tweezers are desirable for implementing the present invention because they allow highly efficient, automated selection (sorting) of neural stem cells. FACS and MACS are particularly preferable because they allow highly precise selection.

The presence or absence of a characteristics property of the neural stem cells (typically expression of a neural stem cell marker gene, or a physiological characteristic of neural stem cells) can be evaluated to verify that the cells produced by the method disclosed here are actually neural stem cells. For example, conventional methods can be used to verify expression of at least the nestin gene, which is a typical example of a neural stem cell marker gene (or preferably expression of both nestin and GFAP), or in other words to verify the presence of the gene products of these neural stem cell marker genes (typically mRNA or proteins (marker proteins)). The mRNA can be verified by PCR (preferably RT-PCR) for example, while the proteins can be verified by immunological methods (such as immune cell staining, Western blotting and flow cytometry).

With the method for producing neural stem cells disclosed here, neural stem cells (or a tissue, organ or the like containing such cells) can be efficiently produced (typically, with high production efficiency) from fibroblasts present in vitro or in vivo by a relatively simple process of supplying a synthetic peptide with a relatively simple structure to fibroblasts. In particular, by using the composition for producing neural stem cells (neural stem cell-inducing synthetic peptide) disclosed here, it is possible to prepare neural stem cells from fibroblasts without using large quantities of liquid factors (such as neural stem cell differentiation-inducing factors, typically retinoic acid and the like) (typically, without using such liquid factors, or by reducing the amount used) such as are used in preparing neural stem cells by inducing differentiation from pluripotent stem cells (such as iPS cells). In other words, neural stem cell production costs can be reduced.

Moreover, in the method for producing neural stem cells disclosed here, neural stem cells can be produced from fibroblasts by supplying an artificially synthesized peptide such as that described above to target fibroblasts. That is, because the method for producing neural stem cells disclosed here does not require gene introduction, there is no risk that an exogenous gene will be inserted into the genome of the resulting neural stem cells. It is thus possible to reduce (typically, to avoid) the risk of cancerization due to insertion of an exogenous gene into the genome. It is also possible to avoid the complex operation of inserting a specific gene into target cells, and reduce the costs associated with gene introduction.

With the method for producing neural stem cells disclosed here, moreover, neural stem cells can be produced without an intervening step of converting fibroblasts to pluripotent stem cells. In other words, fibroblasts can be (directly) transdifferentiated (fate transformed) into neural stem cells (that is, fibroblasts can be directly reprogrammed into neural stem cells). Therefore, neural stem cells can be produced from fibroblasts in fewer steps than when fibroblasts are reprogrammed into pluripotent stem cells, which are then induced to differentiate into neural stem cells. This makes it possible to produce neural stem cells with high reproducibility, and to reduce the time required for producing neural stem cells.

Moreover, because fibroblasts can be transdifferentiated (direct reprogrammed) into neural stem cells without first becoming pluripotent stem cells in the method of producing neural stem cells disclosed here, it is possible to reduce (typically avoid) the risk that undifferentiated pluripotent stem cells will contaminate the cell culture containing the neural stem cells. It is thus possible to reduce (typically avoid) the risk of teratomas (cancerization), which can occur when undifferentiated pluripotent stem cells are transplanted into a living body.

By applying the composition for producing neural stem cells (neural stem cell-inducing synthetic peptide) disclosed here to an in vitro culture system (typically, by adding it to medium of a cell culture), it is possible to efficiently produce neural stem cells (or a tissue or organ or the like containing such cells) from fibroblasts (typically human-derived fibroblasts) cultured (passaged) in vitro. It is also possible to efficiently produce neural stem cells (or a tissue or organ or the like containing such cells) by supplying a suitable amount of the composition for producing nerve cells (nerve cell-inducing synthetic peptide) to a cell material, or in other words to a living tissue or cell mass (such as a culture of fibroblasts derived from a living body), that has been removed either temporarily or permanently from a living body. That is, neural stem cells (or a tissue containing such cells, or a tissue body or the like produced by proliferating and inducing differentiation of neural stem cells) can be produced efficiently in vitro by using the method for producing neural stem cells (method for inducing neural stem cells from fibroblasts) disclosed here.

Effective repair or regeneration can be achieved by returning the neural stem cells (or a tissue containing such cells, or a tissue body or the like produced by proliferating and inducing differentiation of neural stem cells) thus produced in vitro to an affected area (the living body of a patient) requiring such repair or regeneration. That is, it is possible to efficiently treat various diseases for which tissue regeneration is an effective treatment. For example, by transferring neural stem cells produced in vitro by the production method disclosed here into an affected area (the living body of a patient), it is possible to treat Parkinson's disease, cerebral infarction, Alzheimer's disease, paralysis caused by spinal damage, cerebral contusion, amyotrophic lateral sclerosis, Huntington's disease, brain tumors, retinal degeneration and other neurological diseases and injuries for example by a regenerative medicine approach. Moreover, neural stem cells produced in vitro by implementing the method for producing neural stem cells disclosed here can be used as medical materials in regenerative medicine therapies. Moreover, problems of donor insufficiency and rejection reactions can be resolved by producing neural stem cells using fibroblasts obtained from the same test subject (patient).

The desired amount of the composition for producing neural stem cells (neural stem cell-inducing synthetic peptide) disclosed here can also be supplied in vivo (typically to a patient) in the form of a medicinal liquid for example, or in a pill or other solid form, or as an ointment, gel or aqueous jelly. The administration method is not particularly limited, and may be by intravenous, intra-arterial, intradermal, subdermal or intraperitoneal injection for example, or by oral, inhalation, transdermal, transmucosal, or suppository administration or the like. Subdermal, muscular, intracerebral (typically submeningeal (subdural or subarachnoid)) or other implantation of an implantable preparation is another possible method of administration.

Neural stem cells can thus be generated (produced) in vivo, typically from fibroblasts in or around an affected area or from fibroblasts capable of migrating to the affected area. It is thus possible to use these neural stem cells to effectively restore neural function lost due to various kinds of neurological disease or injury. It is thus possible to treat Parkinson's disease, cerebral infarction, Alzheimer's disease, paralysis caused by spinal damage, cerebral contusion, amyotrophic lateral sclerosis, Huntington's disease, brain tumors, retinal degeneration and other neurological diseases and injuries for example by a regenerative medicine approach. In other words, the composition for producing neural stem cells disclosed here can be used as a medicinal composition (pharmaceutical composition) contributing to regenerative medicine therapy for neurological disease and injury. Neural stem cells for transplantation can also be prepared in vivo in animals other than humans (typically, mammals other than humans).

By using neural stem cells produced in large quantities in vitro (in an in vitro culture) and nerve cells that have been induced to differentiate from these neural stem cells to evaluate the toxicity and effectiveness of drugs, it is possible to increase the efficiency and precision of drug evaluation, and reduce associated costs. Moreover, neural stem cells produced in large quantities in vitro (in an in vitro culture) and nerve cells that have been induced to differentiate from these neural stem cells can also be used to produce biological compounds derived from such cells, typically including secretory proteins, hormones and other physiological substances (such as neuropeptides and other neurosecretory hormones, specifically pituitary hormones, subthalamic hormones and the like).

Evaluations that were difficult to implement in the past can now be achieved by testing using neural stem cells produced in large quantities in vitro (in an in vitro culture) and nerve cells that have been induced to differentiate from these neural stem cells. For example, for elucidating the pathology of a diseased area or in the field of therapeutic drug research and development, efficient research can be achieved by using neural stem cells produced from human fibroblasts.

Some examples of the present invention are explained below, but it is not intended that the present invention is limited by these examples.

Example 1: Peptide Synthesis

A synthetic peptide comprising the amino acid sequence of SEQ ID NO:26 above was produced using the peptide synthesizer described below. In the following explanations, this synthetic peptide is called Sample 1. In this synthetic peptide, the carboxyl group (—COOH) of the C-terminal amino acid has been amidated (—CONH$_2$).

The peptide of Sample 1 was synthesized by solid-phase synthesis (Fmoc method) using a commercial peptide synthesizer (Intavis AG) in accordance with the manual. The mode of use of the peptide synthesizer is not explained in detail because it is not a feature of the invention.

The synthesized peptide was dissolved in DMSO to prepare a stock solution.

Example 2: Test to Evaluate Neural Stem Cell-Inducing Activity of Neural Stem Cell-Inducing Synthetic Peptide Neural stem cells were induced (prepared) from fibroblasts using the neural stem cell-inducing synthetic peptide (Sample 1) obtained in Example 1 above. The test cells were CCD1079SK cells (ATCC™ CRL-2097), a cultured cell line of fibroblasts from human skin tissue. The test details were as follows.

Previously frozen CCD1079SK cells were seeded to a cell density of $1.2×10^5$/well in a cell culture chamber (also called a slide chamber). The cell culture chamber had one well per slide (culture area 19 mm×44 mm). Specifically, the thawed CCD1079SK cells were suspended in ordinary Dulbecco's modified Eagle's medium (DMEM) to prepare a cell suspension with a cell density of $1.2×10^5$/mL, and 1 mL of this cell suspension was seeded in the aforementioned cell culture chamber. The DMEM medium was ordinary DMEM (Wako Pure Chemical Industries, Ltd., Cat. No. 043-30085) with 10% FBS, 100 units/mL penicillin and 100 μg/mL streptomycin added thereto. The CCD1079SK cells seeded in the cell culture chamber were pre-cultured for several hours (about six hours) until the cells adhered to the bottom of the culture container in the incubator under conditions of 5% $CO_2$, 37° C.

Following the several hours of pre-culture, the medium of the CCD1079SK cells (cell culture) was replaced with DMEM medium containing 10% FBS, 100 units/mL penicillin and 100 μg/mL streptomycin in addition to the peptide of Sample 1 added to a concentration of 10 μM, and main cultured under conditions of 5% $CO_2$, 30° C. During this main culture, the medium was replaced with the aforementioned DMEM medium containing 10% FBS, 100 units/mL penicillin and 100 μg/mL streptomycin as well as the peptide of Sample 1 at a concentration of 10 μM on the 4th, 6th, 8th, 10th, 13th and 18th day after initiation of culture in the presence of the peptide.

A peptide-free group in which no peptide was added to the medium was established as a control group. As in the peptide group above, the medium in this peptide-free group was replaced with DMEM medium containing 10% FBS, 100 units/mL penicillin and 100 μg/mL streptomycin on the 4th, 6th, 8th, 10th, 13th and 18th day after initiation of culture.

Expression of the neural stem cell marker proteins nestin and GFAP in the cells of each test group was investigated 18 days after initiation of main culture (culture in the presence of the peptide) by the following cell immunostaining (fluorescent immunostaining).

First, the cells in each test group were fixed, permeabilized and blocked. Specifically, the medium was removed from the culture container (slide chamber) of each test group after completion of 18 days of culture in the presence of the peptide, and the cells in each slide chamber were washed with cool PBS. Next, PBS containing 4 vol % paraformaldehyde (4% paraformaldehyde solution) was added to each slide chamber, and the cells were fixed by standing for 15 minutes on ice. After a specific amount of time, the 4% paraformaldehyde solution was removed, and the cells in each slide chamber were washed with cool PBS.

Next, PBS containing 0.25 vol % Triton™ X-100 (this solution is called "PBS-T" below) was added to each slide chamber, and the cells were left standing for 30 minutes at room temperature to permeabilize the cell membranes. After a specific amount of time the PBS-T was removed, and the cells in each slide chamber were washed with cool PBS.

PBS containing 1% BSA (1% BSA-containing PBS) was then added to each slide chamber, and the cells were blocked for one hour at room temperature. After a specific amount of time, the PBS containing 1% BSA was removed, and the cells in each slide chamber were washed with cool PBS.

Next, cell immunostaining was performed with an anti-nestin antibody and a secondary antibody recognizing that antibody, or with an anti-GFAP antibody and a secondary antibody recognizing that antibody.

Specifically, the cells in each test group were stained for the nestin protein as follows. A primary antibody dilution obtained by diluting an anti-nestin antibody (Abcam plc. rabbit antibody, Cat. No. ab92391) 250 times with PBS containing 1% BSA was added to the slide chamber, and left standing overnight (about 16 to 18 hours) at 4° C. After a specific amount of time, the primary antibody dilution was removed, and the cells were washed three times with cool PBS. Next, an anti-rabbit IgG antibody (Life Technologies goat antibody, A-11008) labeled with a fluorescent dye (Alexa Fluor™ 488) was added to the slide chamber as a secondary antibody, and left standing in the dark for 1 hour at room temperature. After a specific amount of time, the secondary antibody dilution was removed, and the cells were washed three times with cool PBS. The cells that had been subjected to this cell immunostaining in each test group were then mounted with a cover glass and Slow Fade (Life Technologies, Cat. No. S36946), a mountant containing DAPI.

The cells in each test group were also stained as follows for GFAP. First, a primary antibody dilution obtained by diluting anti-GFAP antibody (Abcam plc. rabbit antibody, Cat. No. ab7260) 1000 times with PBS containing 1% BSA was added inside the slide chamber, and left standing overnight (about 16 to 18 hours) at 4° C. After a specific amount of time, the primary antibody dilution was removed, and the cells were washed three times with cool PBS. Next, an anti-rabbit IgG antibody (Thermo Fisher Scientific Inc. goat antibody, A-21428) labeled with a fluorescent dye (Alexa Fluor™ 555) was added to the slide chamber as a secondary antibody, and left standing in the dark for one hour at room temperature. After a specific amount of time, the secondary antibody dilution was removed, and the cells were washed three times with cool PBS. The cells that had been subjected to this cell immunostaining in each test group were then mounted with a cover glass and Slow Fade (Life Technologies, Cat. No. S36946), a mountant containing DAPI.

The cells that had been subjected to cell immunostaining (fluorescent immunostatining) in each test group as described above were then subject to fluorescent observation by confocal laser microscopy.

Figure 2:
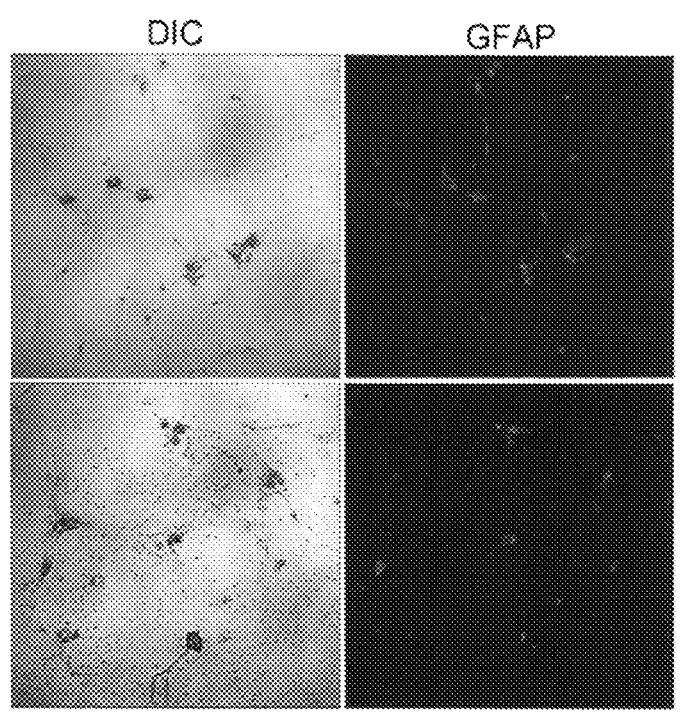
FIG. 2 shows microscope photographs (images) of fibroblast morphology and GFAP expression after 18 days of culture in the presence of a neural stem cell-inducing synthetic peptide (Sample 1) of one embodiment. The photographs (images) in the DIC column (left column) are optical microscope photographs (images) showing fibroblast morphology, while the photographs (images) in the GFAP column (right column) are fluorescence microscope photographs (images) showing expression of GFAP in the same fibroblasts (same visual field)
Figure 3:
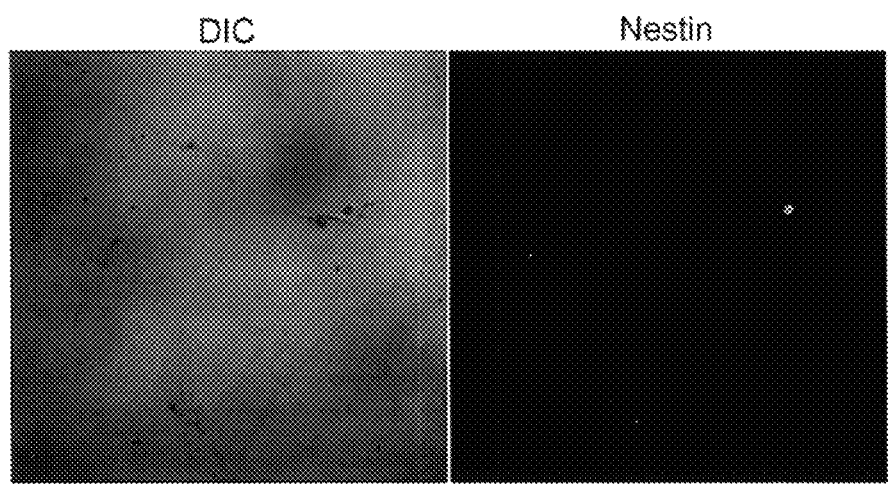
FIG. 3 shows microscope photographs (images) of fibroblast morphology and nestin protein expression after 18 days of culture without addition of a neural stem cell-inducing synthetic peptide. The left hand photograph (image) is an optical microscope photograph (image) showing fibroblast morphology, and the right hand photograph (image) is a fluorescence microscope photograph (image) showing nestin expression in the same fibroblasts (same visual field)
Figure 4:
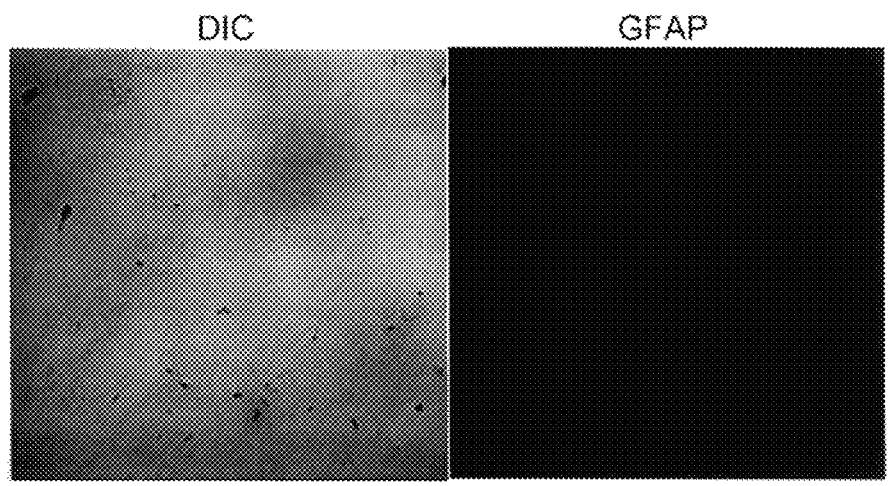
FIG. 4 shows microscope photographs (images) of fibroblast morphology and GFAP expression after 18 days of culture without additional of a neural stem cell-inducing synthetic peptide. The left hand photograph (image) is an optical microscope photograph (image) showing fibroblast morphology, and the right hand photograph (image) is a fluorescence microscope photograph (image) showing GFAP expression in the same fibroblasts (same visual field).

The results of fluorescent observation by confocal laser microscopy are shown in FIG. 1 to FIG. 4. These figures are fluorescent microscope photographs showing expression of the nestin protein or GFAP in each test group, with fluorescent images showing the results for expression of the nestin protein or GFAP by the immunofluorescent antibody technique shown in the right column, and images (photographs) showing the results of optical microscopy (differential interference microscopy) of the same field as in the fluorescent microscopy shown in the left column. FIG. 1 and FIG. 2 show results in the Sample 1 group, while FIG. 3 and FIG. 4 show results for the peptide-free group.

As shown in FIG. 1 and FIG. 2, the Sample 1 group was confirmed to have more cells with increased quantities of nestin protein and GFAP in comparison with the peptide-free groups (FIG. 3 and FIG. 4). That is, the Sample 1 group had more cells with increased expression of the neural stem cell marker genes nestin and GFAP. This indicates the presence of neural stem cells (typically nestin expressing cells, such as cells co-expressing nestin and GFAP) in the Sample 1 group, to which the peptide of Sample 1 was added.

These results show that fibroblasts can be induced to differentiate into neural stem cells (typically nestin-expressing cells, such as cells co-expressing nestin and GFAP), or in other words that neural stem cells (typically nestin-expressing cells, such as cells co-expressing nestin and GFAP) can be produced with the method disclosed here. No step of preparing pluripotent stem cells was required in producing neural stem cells from those fibroblasts. That is, these results show that (direct) transdifferentiation (that is, direct reprogramming) of fibroblasts into neural stem cells (typically nestin-expressing cells, such as cells co-expressing nestin and GFAP) is possible with the method disclosed here.

These results also show that the neural stem cell-inducing synthetic peptide disclosed here (and a neural stem cell differentiation inducer having this peptide as an active ingredient) is a peptide (composition) capable of inducing differentiation of fibroblasts into neural stem cells (typically nestin-expressing cells, such as cells co-expressing nestin and GFAP).

Example 3: Preparation of Granules 50 mg of the synthetic peptide (neural stem cell-inducing synthetic peptide) of Sample 1 was mixed with 50 mg of crystalline cellulose and 400 mg of lactose, 1 mL of a mixed solution of ethanol and water was added, and the mixture was kneaded. The kneaded product was granulated by conventional methods to obtain granules (a granular composition) having the neural stem cell-inducing synthetic peptide disclosed here as its primary ingredient.

INDUSTRIAL APPLICABILITY

As discussed above, the neural stem cell-inducing synthetic peptide disclosed here has the neural stem cell inducing ability to differentiate fibroblasts into neural stem cells. Therefore, it can be used favorably with the aim of inducing target fibroblasts (especially human fibroblasts) to differentiate into neural stem cells. Thus, the composition for producing neural stem cells disclosed here can be used favorably as a composition for regenerative medicine for example.

With the method for producing neural stem cells disclosed here, neural stem cells can be prepared from fibroblasts without an intervening step of preparing pluripotent stem cells. It is thus possible to produce neural stem cells efficiently from fibroblasts. The neural stem cells produced by this method can be used favorably as a cell resource for regenerative medicine.

SEQUENCE TABLE FREE TEXT

SEQ ID NOS:1 to 26 Synthetic peptides

What is claimed is:

1. A method for producing neural stem cells from fibroblasts, comprising:
   preparing a cell culture of the fibroblasts,
      wherein the fibroblasts are cultured independently without co-cultivation with other cells; and
   supplying an artificially produced synthetic peptide to the cell culture,
      wherein the synthetic peptide comprises:
         a) the amino acid sequence of LLLLLLVGLTAPA (SEQ ID NO:16); and
         b) a transmembrane peptide sequence of KKRTLRKNDRKKR (SEQ ID NO:7);
      and wherein the total number of amino acid residues constituting the synthetic peptide is 50 or fewer.

2. The production method according to claim 1, wherein the transmembrane peptide sequence is disposed adjacent to the N-end or C-end of the amino acid sequence of LLLLLLVGLTAPA (SEQ ID NO:16).

3. The production method according to claim 1, wherein a linker sequence consisting of one, two or three glycine residues is disposed between the amino acid sequence of LLLLLLVGLTAPA (SEQ ID NO:16) and the transmembrane peptide sequence.

4. The production method according to claim 1, wherein the synthetic peptide comprises the following amino acid sequence:
   LLLLLLVGLTAPAGKKRTLRKNDRKKR (SEQ ID NO:26).

5. The production method according to claim 1, wherein the fibroblasts are fibroblasts derived from human skin.

6. A method for producing neural stem cells from fibroblasts, comprising:
   preparing a cell culture containing the fibroblasts; and
   supplying an artificially produced synthetic peptide to the cell culture,
      wherein the synthetic peptide comprises:
         a) the amino acid sequence of LLLLLLVGLTAPA (SEQ ID NO:16); and
         b) a transmembrane peptide sequence of KKRTLRKNDRKKR (SEQ ID NO:7);
      wherein the total number of amino acid residues constituting the synthetic peptide is 50 or fewer, and
      wherein the fibroblasts are fibroblasts derived from human skin.

* * * * *

SEQUENCE LISTING

```
<160> NUMBER OF SEQ ID NOS: 26

<210> SEQ ID NO 1
<211> LENGTH: 29
<212> TYPE: PRT
<213> ORGANISM: Artificial sequence
<220> FEATURE:
<223> OTHER INFORMATION: Synthetic peptide

<400> SEQUENCE: 1

Met Ala Ala Thr Gly Thr Ala Ala Ala Ala Thr Gly Arg Leu Leu
1               5                   10                  15

Leu Leu Leu Leu Val Gly Leu Thr Ala Pro Ala Leu Ala
                20                  25

<210> SEQ ID NO 2
<211> LENGTH: 29
<212> TYPE: PRT
<213> ORGANISM: Artificial sequence
<220> FEATURE:
<223> OTHER INFORMATION: Synthetic peptide

<400> SEQUENCE: 2

Met Ala Ala Thr Gly Thr Ala Ala Ala Ala Thr Gly Lys Leu Leu
1               5                   10                  15

Val Leu Leu Leu Leu Gly Leu Thr Ala Pro Ala Ala Ala
                20                  25

<210> SEQ ID NO 3
<211> LENGTH: 38
<212> TYPE: PRT
<213> ORGANISM: Artificial sequence
<220> FEATURE:
<223> OTHER INFORMATION: Synthetic peptide

<400> SEQUENCE: 3

Met Gly Pro Ala Ser Pro Ala Ala Arg Gly Leu Ser Arg Arg Pro Gly
1               5                   10                  15
```

Gln Pro Pro Leu Pro Leu Leu Leu Pro Leu Leu Leu Leu Leu Arg
            20                  25                  30

Ala Gln Pro Ala Ile Gly
        35

<210> SEQ ID NO 4
<211> LENGTH: 37
<212> TYPE: PRT
<213> ORGANISM: Artificial sequence
<220> FEATURE:
<223> OTHER INFORMATION: Synthetic peptide

<400> SEQUENCE: 4

Met Gly Pro Thr Ser Pro Ala Ala Arg Gly Gln Gly Arg Arg Trp Arg
1               5                   10                  15

Pro Pro Leu Pro Leu Leu Leu Pro Leu Ser Leu Leu Leu Arg Ala
            20                  25                  30

Gln Leu Ala Val Gly
        35

<210> SEQ ID NO 5
<211> LENGTH: 17
<212> TYPE: PRT
<213> ORGANISM: Artificial sequence
<220> FEATURE:
<223> OTHER INFORMATION: Synthetic peptide

<400> SEQUENCE: 5

Met Leu Pro Gly Leu Ala Leu Leu Leu Ala Ala Trp Thr Ala Arg
1               5                   10                  15

Ala

<210> SEQ ID NO 6
<211> LENGTH: 17
<212> TYPE: PRT
<213> ORGANISM: Artificial sequence
<220> FEATURE:
<223> OTHER INFORMATION: Synthetic peptide

<400> SEQUENCE: 6

Met Leu Pro Ser Leu Ala Leu Leu Leu Ala Ala Trp Thr Val Arg
1               5                   10                  15

Ala

<210> SEQ ID NO 7
<211> LENGTH: 13
<212> TYPE: PRT
<213> ORGANISM: Artificial sequence
<220> FEATURE:
<223> OTHER INFORMATION: synthetic peptide

<400> SEQUENCE: 7

Lys Lys Arg Thr Leu Arg Lys Asn Asp Arg Lys Lys Arg
1               5                   10

<210> SEQ ID NO 8
<211> LENGTH: 14
<212> TYPE: PRT
<213> ORGANISM: Artificial sequence
<220> FEATURE:
<223> OTHER INFORMATION: Synthetic peptide

<400> SEQUENCE: 8

Arg Ser Arg Lys Tyr Thr Ser Trp Tyr Val Ala Leu Lys Arg
1               5                   10

<210> SEQ ID NO 9
<211> LENGTH: 8
<212> TYPE: PRT
<213> ORGANISM: Artificial sequence
<220> FEATURE:
<223> OTHER INFORMATION: Synthetic peptide

<400> SEQUENCE: 9

Trp Arg Arg Gln Ala Arg Phe Lys
1               5

<210> SEQ ID NO 10
<211> LENGTH: 13
<212> TYPE: PRT
<213> ORGANISM: Artificial sequence
<220> FEATURE:
<223> OTHER INFORMATION: Synthetic peptide

<400> SEQUENCE: 10

Arg Leu Pro Val Arg Arg Arg Arg Arg Val Pro Lys
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic peptide

<400> SEQUENCE: 11

Tyr Gly Arg Lys Lys Arg Arg Gln Arg Arg
1               5                   10

<210> SEQ ID NO 12
<211> LENGTH: 11
<212> TYPE: PRT
<213> ORGANISM: Artificial sequence
<220> FEATURE:
<223> OTHER INFORMATION: Synthetic peptide

<400> SEQUENCE: 12

Tyr Ala Arg Ala Ala Arg Gln Ala Arg Ala
1               5                   10

<210> SEQ ID NO 13
<211> LENGTH: 16
<212> TYPE: PRT
<213> ORGANISM: Artificial sequence
<220> FEATURE:
<223> OTHER INFORMATION: Synthetic peptide

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

Arg Arg Arg Arg Arg Arg Arg Arg Arg

```
<210> SEQ ID NO 15
<211> LENGTH: 19
<212> TYPE: PRT
<213> ORGANISM: Artificial sequence
<220> FEATURE:
<223> OTHER INFORMATION: Synthetic peptide

<400> SEQUENCE: 15

Gly Arg Cys Arg Arg Leu Ala Asn Phe Pro Gly Arg Lys Arg Arg
1               5                   10                  15

Arg Arg Arg

<210> SEQ ID NO 16
<211> LENGTH: 13
<212> TYPE: PRT
<213> ORGANISM: Artificial sequence
<220> FEATURE:
<223> OTHER INFORMATION: Synthetic peptide

<400> SEQUENCE: 16

Leu Leu Leu Leu Leu Leu Val Gly Leu Thr Ala Pro Ala
1               5                   10

<210> SEQ ID NO 17
<211> LENGTH: 12
<212> TYPE: PRT
<213> ORGANISM: Artificial sequence
<220> FEATURE:
<223> OTHER INFORMATION: Synthetic peptide

<400> SEQUENCE: 17

Leu Val Leu Leu Leu Leu Gly Leu Thr Ala Pro Ala
1               5                   10

<210> SEQ ID NO 18
<211> LENGTH: 13
<212> TYPE: PRT
<213> ORGANISM: Artificial sequence
<220> FEATURE:
<223> OTHER INFORMATION: Synthetic peptide

<400> SEQUENCE: 18

Pro Leu Pro Leu Leu Leu Pro Leu Leu Leu Leu Leu Leu
1               5                   10

<210> SEQ ID NO 19
<211> LENGTH: 13
<212> TYPE: PRT
<213> ORGANISM: Artificial sequence
<220> FEATURE:
<223> OTHER INFORMATION: Synthetic peptide

<400> SEQUENCE: 19

Leu Leu Leu Leu Leu Leu Arg Ala Gln Pro Ala Ile Gly
1               5                   10

<210> SEQ ID NO 20
<211> LENGTH: 13
<212> TYPE: PRT
<213> ORGANISM: Artificial sequence
<220> FEATURE:
<223> OTHER INFORMATION: Synthetic peptide

<400> SEQUENCE: 20
```

Pro Leu Pro Leu Leu Pro Leu Ser Leu Leu Leu Leu
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic peptide

<400> SEQUENCE: 21

Leu Ser Leu Leu Leu Leu Arg Ala Gln Leu Ala Val Gly
1               5                   10

<210> SEQ ID NO 22
<211> LENGTH: 14
<212> TYPE: PRT
<213> ORGANISM: Artificial sequence
<220> FEATURE:
<223> OTHER INFORMATION: Synthetic peptide

<400> SEQUENCE: 22

Met Leu Pro Gly Leu Ala Leu Leu Leu Leu Ala Ala Trp Thr
1               5                   10

<210> SEQ ID NO 23
<211> LENGTH: 15
<212> TYPE: PRT
<213> ORGANISM: Artificial sequence
<220> FEATURE:
<223> OTHER INFORMATION: Synthetic peptide

<400> SEQUENCE: 23

Pro Gly Leu Ala Leu Leu Leu Leu Ala Ala Trp Thr Ala Arg Ala
1               5                   10                  15

<210> SEQ ID NO 24
<211> LENGTH: 14
<212> TYPE: PRT
<213> ORGANISM: Artificial sequence
<220> FEATURE:
<223> OTHER INFORMATION: Synthetic peptide

<400> SEQUENCE: 24

Met Leu Pro Ser Leu Ala Leu Leu Leu Leu Ala Ala Trp Thr
1               5                   10

<210> SEQ ID NO 25
<211> LENGTH: 15
<212> TYPE: PRT
<213> ORGANISM: Artificial sequence
<220> FEATURE:
<223> OTHER INFORMATION: Synthetic peptide

<400> SEQUENCE: 25

Pro Ser Leu Ala Leu Leu Leu Leu Ala Ala Trp Thr Val Arg Ala
1               5                   10                  15

<210> SEQ ID NO 26
<211> LENGTH: 27
<212> TYPE: PRT
<213> ORGANISM: Artificial sequence

```
<220> FEATURE:
<223> OTHER INFORMATION: Synthetic peptide

<400> SEQUENCE: 26

Leu Leu Leu Leu Leu Leu Val Gly Leu Thr Ala Pro Ala Gly Lys Lys
1               5                   10                  15

Arg Thr Leu Arg Lys Asn Asp Arg Lys Lys Arg
            20                  25
```